United States Patent
Sogo et al.

(10) Patent No.: US 6,197,547 B1
(45) Date of Patent: Mar. 6, 2001

(54) TRIGGER FACTOR EXPRESSION PLASMIDS

(75) Inventors: Kazuyo Sogo, Kyoto; Hideki Yanagi, Takarazuka; Takashi Yura, Kyoto, all of (JP)

(73) Assignee: HSP Research Institute, Inc., Osaka (JP)

( * ) Notice: Subject to any disclaimer, the term of this patent is extended or adjusted under 35 U.S.C. 154(b) by 0 days.

(21) Appl. No.: 09/472,971

(22) Filed: Dec. 28, 1999

(30) Foreign Application Priority Data

Dec. 28, 1998 (JP) .................................... 10-372965

(51) Int. Cl.⁷ .......................... C12N 15/63; C12N 15/31; C12N 1/21; C12P 21/06
(52) U.S. Cl. ................. 435/69.1; 435/320.1; 435/252.3; 435/252.33; 536/23.1; 536/24.1
(58) Field of Search .............................. 435/69.1, 320.1, 435/252.3, 252.33; 536/23.1, 24.1

(56) References Cited

PUBLICATIONS

Hartl, Nature 381: 571–580, Molecular chaperones in cellular protein folding, Jun. 1996.*
Wall et al., Current Opinion in Biotechnology 6: 507–516, Effects of overexpressing folding modulators on the in vivo folding of heterologous proteins in *E. coli*, 1995.*
Thomas, Jeffrey G. et al., Applied Biochemistry and Biotechnology, vol. 66 (1997) pp. 198–238.
Yasukawa, Takashi et al., The Journal of Biological Chemistry, vol. 270, No. 43 (1995) pp. 25328–25331.
Crooke et al., *Proc. Natl. Acad. Sci.*, USA, vol. 84, pp. 5216–5220 (Aug. 1987).
Guthrie et al., *Journal of Bacteriology*, vol. 172, No. 10, pp. 5555–5562 (Oct. 1990).
Callebaut et al., *FEBS Letter*, vol. 374, pp. 211–215 (1995).
Stoller et al., *The EMBO Journal*, vol. 14, No. 20, pp. 4939–4948 (1995).
Valent et al., *The EMBO Journal*, vol. 14, No. 22, pp. 5494–5505 (1995).
Hesterkamp et al., *Proc. Natl. Acad. Sci.* USA, vol. 93, pp. 4437–4441 (Apr. 1996).
Kandror et al., *The EMBO Journal*, vol.14, No. 23, pp. 6021–6027 (1995).
Kandror et al., *The Journal of Biologocial Chemistry*, vol. 272, No. 3, pp. 1730–1734 (Jan. 1997).
Scholz et al., *The EMBO Journal*, vol. 16, No. 1, pp. 54–58 (1997).
Kohara et al., *Cell*, vol. 50, pp. 495–508 (Jul. 31, 1987).
Hemmingsen et al., *Nature*, vol. 333, pp. 330–334 (1988).
Nishihara et al., *Appl. Environ. Microbiol.*, vol. 64, pp. 1694–1699 (1988).
Perez–Perez et al., *Gene*, vol. 158, pp. 141–142 (1995).
O'Reilly et al., *Cell*, vol. 88, pp. 277–285 (Jan. 24, 1997).

* cited by examiner

*Primary Examiner*—Robert A. Schwartzman
*Assistant Examiner*—Katharine F Davis
(74) *Attorney, Agent, or Firm*—Birch, Stewart, Kolasch & Birch, LLP

(57) ABSTRACT

An artificial operon comprising genes encoding each of a trigger factor, GroEL and GroES, an expression plasmid carrying the operon, an expression plasmid carrying a gene encoding the trigger factor, a cotransformant harboring an expression vector for a foreign protein and any one of the expression plasmids, and a method for producing a foreign protein comprising expressing a foreign protein by the use of the cotransformant, which are capable of expressing a foreign protein in a solubilized form and in a state of having a correct conformation.

25 Claims, 4 Drawing Sheets

SEQUENCE LISTING

<160> NUMBER OF SEQ ID NOS: 7

<210> SEQ ID NO 1
<211> LENGTH: 432
<212> TYPE: PRT
<213> ORGANISM: Escherichia coli

<400> SEQUENCE: 1

```
Met Gln Val Ser Val Glu Thr Thr Gln Gly Leu Gly Arg Arg Val Thr
 1               5                  10                  15

Ile Thr Ile Ala Ala Asp Ser Ile Glu Thr Ala Val Lys Ser Glu Leu
                20                  25                  30

Val Asn Val Ala Lys Lys Val Arg Ile Asp Gly Phe Arg Lys Gly Lys
            35                  40                  45

Val Pro Met Asn Ile Val Ala Gln Arg Tyr Gly Ala Ser Val Arg Gln
        50                  55                  60

Asp Val Leu Gly Asp Leu Met Ser Arg Asn Phe Ile Asp Ala Ile Ile
 65                  70                  75                  80

Lys Glu Lys Ile Asn Pro Ala Gly Ala Pro Thr Tyr Val Pro Gly Glu
                85                  90                  95

Tyr Lys Leu Gly Glu Asp Phe Thr Tyr Ser Val Glu Phe Glu Val Tyr
               100                 105                 110

Pro Glu Val Glu Leu Glu Gly Leu Glu Ala Ile Glu Val Glu Lys Pro
           115                 120                 125

Ile Val Glu Val Thr Asp Ala Asp Val Asp Gly Met Leu Asp Thr Leu
       130                 135                 140

Arg Lys Gln Gln Ala Thr Trp Lys Glu Lys Asp Gly Ala Val Glu Ala
145                 150                 155                 160
```

-continued

```
Glu Asp Arg Val Thr Ile Asp Phe Thr Gly Ser Val Asp Gly Glu Glu
                165                 170                 175
Phe Glu Gly Gly Lys Ala Ser Asp Phe Val Leu Ala Met Gly Gln Gly
            180                 185                 190
Arg Met Ile Pro Gly Phe Glu Asp Gly Ile Lys Gly His Lys Ala Gly
        195                 200                 205
Glu Glu Phe Thr Ile Asp Val Thr Phe Pro Glu Glu Tyr His Ala Glu
    210                 215                 220
Asn Leu Lys Gly Lys Ala Ala Lys Phe Ala Ile Asn Leu Lys Lys Val
225                 230                 235                 240
Glu Glu Arg Glu Leu Pro Glu Leu Thr Ala Glu Phe Ile Lys Arg Phe
                245                 250                 255
Gly Val Glu Asp Gly Ser Val Glu Gly Leu Arg Ala Glu Val Arg Lys
            260                 265                 270
Asn Met Glu Arg Glu Leu Arg Ala Pro Ser Val Thr Ala Leu Ser Ser
        275                 280                 285
Gln Ala Ile Glu Gly Leu Val Lys Ala Asn Asp Ile Asp Val Pro Ala
    290                 295                 300
Ala Leu Ile Asp Ser Glu Ile Asp Val Leu Arg Arg Gln Ala Ala Gln
305                 310                 315                 320
Arg Phe Gly Gly Asn Glu Lys Gln Ala Leu Glu Leu Pro Arg Glu Leu
                325                 330                 335
Phe Glu Glu Gln Ala Lys Arg Arg Val Val Gly Leu Leu Leu Gly
            340                 345                 350
Glu Val Ile Arg Thr Asn Glu Leu Lys Ala Asp Glu Glu Arg Val Lys
        355                 360                 365
Gly Leu Ile Glu Glu Met Ala Ser Ala Tyr Glu Asp Pro Lys Glu Val
    370                 375                 380
Ile Glu Phe Tyr Ser Lys Asn Lys Glu Leu Met Asp Asn Met Arg Asn
385                 390                 395                 400
Val Ala Leu Glu Glu Gln Ala Val Glu Ala Val Leu Ala Lys Ala Lys
                405                 410                 415
Val Thr Glu Lys Glu Thr Thr Phe Asn Glu Leu Met Asn Gln Gln Ala
            420                 425                 430
```

<210> SEQ ID NO 2
<211> LENGTH: 1299
<212> TYPE: DNA
<213> ORGANISM: Escherichia coli

<400> SEQUENCE: 2

| | |
|---|---|
| atgcaagttt cagttgaaac cactcaaggc cttggccgcc gtgtaacgat tactatcgct | 60 |
| gctgacagca tcgagaccgc tgttaaaagc gagctggtca acgttgcgaa aaaagtacgt | 120 |
| attgacggct tccgcaaagg caaagtgcca atgaatatcg ttgctcagcg ttatggcgcg | 180 |
| tctgtacgcc aggacgttct gggtgacctg atgagccgta acttcattga cgccatcatt | 240 |
| aaagaaaaaa tcaatccggc tggcgcaccg acttatgttc cgggcgaata caagctgggt | 300 |
| gaagacttca cttactctgt agagtttgaa gtttatccgg aagttgaact cgagggtctg | 360 |
| gaagcgatcg aagttgaaaa accgatcgtt gaagtgaccg acgctgacgt tgacggcatg | 420 |
| ctggatactc tgcgtaaaca gcaggcgacc tggaaagaaa agacggcgc tgttgaagca | 480 |
| gaagaccgcg taaccatcga cttcaccggt tctgtagacg gcgaagagtt cgaaggcggt | 540 |
| aaagcgtctg atttcgtact ggcgatgggc cagggtcgta tgatcccggg ctttgaagac | 600 |

-continued

```
ggtatcaaag gccacaaagc tggcgaagag ttcaccatcg acgtgacctt cccggaagaa      660
taccacgcag aaaacctgaa aggtaaagca gcgaaattcg ctatcaacct gaagaaagtt      720
gaagagcgtg aactgccgga actgactgca gaattcatca acgtttcgg cgttgaagat       780 ggttccgtag aaggtctgcg cgctgaagtg cgtaaaaaca tggagcgcga gctgaagagc      840
gccatccgta accgcgttaa gtctcaggcg atcgaaggtc tggtaaaagc taacgacatc      900
gacgtaccgg ctgcgctgat cgacagcgaa atcgacgttc tgcgtcgcca ggctgcacag      960
cgtttcggtg gcaacgaaaa acaagctctg gaactgccgc gcgaactgtt cgaagaacag     1020
gctaaacgcc gcgtagttgt tggcctgctg ctgggcgaag ttatccgcac caacgagctg     1080
aaagctgacg aagagcgcgt gaaaggcctg atcgaagaga tggcttctgc gtacgaagat     1140
ccgaaagaag ttatcgagtt ctacagcaaa aacaaagaac tgatggacaa catgcgcaat     1200
gttgctctgg aagaacaggc tgttgaagct gtactggcga aagcgaaagt gactgaaaaa     1260
gaaaccactt tcaacgagct gatgaaccag caggcgtaa                            1299
```

<210> SEQ ID NO 3
<211> LENGTH: 548
<212> TYPE: PRT
<213> ORGANISM: Escherichia coli

<400> SEQUENCE: 3

```
Met Ala Ala Lys Asp Val Lys Phe Gly Asn Asp Ala Arg Val Lys Met
  1               5                  10                  15

Leu Arg Gly Val Asn Val Leu Ala Asp Ala Val Lys Val Thr Leu Gly
                 20                  25                  30

Pro Lys Gly Arg Asn Val Val Leu Asp Lys Ser Phe Gly Ala Pro Thr
             35                  40                  45

Ile Thr Lys Asp Gly Val Ser Val Ala Arg Glu Ile Glu Leu Glu Asp
         50                  55                  60

Lys Phe Glu Asn Met Gly Ala Gln Met Val Lys Glu Val Ala Ser Lys
 65                  70                  75                  80

Ala Asn Asp Ala Ala Gly Asp Gly Thr Thr Thr Ala Thr Val Leu Ala
                 85                  90                  95

Gln Ala Ile Ile Thr Glu Gly Leu Lys Ala Val Ala Ala Gly Met Asn
                100                 105                 110

Pro Met Asp Leu Lys Arg Gly Ile Asp Lys Ala Val Thr Ala Ala Val
            115                 120                 125

Glu Glu Leu Lys Ala Leu Ser Val Pro Cys Ser Asp Ser Lys Ala Ile
        130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205

Glu Thr Gly Ala Val Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255
```

-continued

Glu Ala Leu Ala Thr Ala Val Val Asn Thr Ile Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Gly Gly Thr Val Ile Ser Glu Glu
    290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg
        355                 360                 365

Val Ala Lys Leu Ala Gly Gly Val Ala Val Ile Lys Val Gly Ala Ala
    370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
            420                 425                 430

Asn Glu Asp Gln Asn Val Gly Ile Lys Val Ala Leu Arg Ala Met Glu
        435                 440                 445

Ala Pro Leu Arg Gln Ile Val Leu Asn Cys Gly Glu Glu Pro Ser Val
    450                 455                 460

Val Ala Asn Thr Val Lys Gly Gly Asp Gly Asn Tyr Gly Tyr Asn Ala
465                 470                 475                 480

Ala Thr Glu Glu Tyr Gly Asn Met Ile Asp Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
        515                 520                 525

Ala Ala Asp Leu Gly Ala Ala Gly Gly Met Gly Gly Met Gly Gly Met
    530                 535                 540

Gly Gly Met Met
545

<210> SEQ ID NO 4
<211> LENGTH: 97
<212> TYPE: PRT
<213> ORGANISM: Escherichia coli

<400> SEQUENCE: 4

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Gly Asn Gly Arg Ile
        35                  40                  45

Leu Glu Asn Gly Glu Val Lys Pro Leu Asp Val Lys Val Gly Asp Ile
    50                  55                  60

Val Ile Phe Asn Asp Gly Tyr Gly Val Lys Ser Glu Lys Ile Asp Asn
65                  70                  75                  80

Glu Glu Val Leu Ile Met Ser Glu Ser Asp Ile Leu Ala Ile Val Glu
            85                  90                  95
Ala

<210> SEQ ID NO 5
<211> LENGTH: 1647
<212> TYPE: DNA
<213> ORGANISM: Escherichia coli

<400> SEQUENCE: 5

| | | | | | | |
|---|---|---|---|---|---|---|
| atggcagcta | aagacgtaaa | attcggtaac | gacgctcgtg | tgaaaatgct | gcgcggcgta | 60 |
| aacgtactgg | cagatgcagt | gaaagttacc | ctcggtccaa | aaggccgtaa | cgtagttctg | 120 |
| gataaatctt | tcggtgcacc | gaccatcacc | aaagatggtg | tttccgttgc | tcgtgaaatc | 180 |
| gaactggaag | acaagttcga | aaatatgggt | gcgcagatgg | tgaaagaagt | tgcctctaaa | 240 |
| gcaaacgacg | ctgcaggcga | cggtaccacc | actgcaaccg | tactggctca | ggctatcatc | 300 |
| actgaaggtc | tgaaagctgt | tgctgcgggc | atgaacccga | tggacctgaa | acgtggtatc | 360 |
| gacaaagcgg | ttaccgctgc | agttgaagaa | ctgaaagcgc | tgtccgtacc | atgctctgac | 420 |
| tctaaagcga | ttgctcaggt | tggtaccatc | tccgctaact | ccgacgaaac | cgtaggtaaa | 480 |
| ctgatcgctg | aagcgatgga | caaagtcggt | aaagaaggcg | ttatcaccgt | tgaagacggt | 540 |
| accggtctgc | aggacgaact | ggacgtggtt | gaaggtatgc | agttcgaccg | tggctacctg | 600 |
| tctccttact | tcatcaacaa | gccggaaact | ggcgcagtag | aactgaaaag | cccgttcatc | 660 |
| ctgctggctg | acaagaaaat | ctccaacatc | cgcgaaatgc | tgccggttct | ggaagctgtt | 720 |
| gccaaagcag | gcaaaccgct | gctgatcatc | gctgaagatg | tagaaggcga | agcgctggca | 780 |
| actgctgttg | ttaacaccat | tcgtggcatc | gtgaaagtcg | ctgcggttaa | agcaccgggc | 840 |
| ttcggcgatc | gtcgtaaagc | tatgctgcag | gatatcgcaa | ccctgactgg | cggtaccgtg | 900 |
| atctctgaag | agatcggtat | ggagctggaa | aaagcaaccc | tggaagacct | gggtcaggct | 960 |
| aaacgtgttg | tgatcaacaa | agacaccacc | actatcatcg | atggcgtggg | tgaagaagct | 1020 |
| gcaatccagg | gccgtgttgc | tcagatccgt | cagcagattg | aagaagcaac | ttctgactac | 1080 |
| gaccgtgaaa | aactgcagga | acgcgtagcg | aaactggcag | gcggcgttgc | agttatcaaa | 1140 |
| gtgggtgctg | ctaccgaagt | tgaaatgaaa | gagaaaaaag | cacgcgttga | agatgccctg | 1200 |
| cacgcgaccc | gtgctgcggt | agaagaaggc | gtggttgctg | gtggtggtgt | tgcgctgatc | 1260 |
| cgcgtagcgt | ctaaactggc | tgacctgcgt | ggtcagaacg | aagaccagaa | cgtgggtatc | 1320 |
| aaagttgcac | tgcgtgcaat | ggaagctccg | ctgcgtcaga | tcgtattgaa | ctgcggcgaa | 1380 |
| gaaccgtctg | ttgttgctaa | caccgttaaa | ggcggcgacg | gcaactacgg | ttacaacgca | 1440 |
| gcaaccgaag | aatacggcaa | catgatcgac | atgggtatcc | tggatccaac | caaagtaact | 1500 |
| cgttctgctc | tgcagtacgc | agcttctgtg | gctggcctga | tgatcaccac | cgaatgcatg | 1560 |
| gttaccgacc | tgccgaaaaa | cgatgcagct | gacttaggcg | ctgctggcgg | tatgggcggc | 1620 |
| atgggtggca | tgggcggcat | gatgtaa | | | | 1647 |

<210> SEQ ID NO 6
<211> LENGTH: 294
<212> TYPE: DNA
<213> ORGANISM: Escherichia coli

<400> SEQUENCE: 6

| | | | | | | |
|---|---|---|---|---|---|---|
| atgaatattc | gtccattgca | tgatcgcgtg | atcgtcaagc | gtaaagaagt | tgaaactaaa | 60 |

-continued

| | |
|---|---|
| tctgctggcg gcatcgttct gaccggctct gcagcggcta atccacccg cggcgaagtg | 120 |
| ctggctgtcg gcaatggccg tatccttgaa atggcgaag tgaagccgct ggatgtgaaa | 180 |
| gttggcgaca tcgttatttt caacgatggc tacggtgtga atctgagaa gatcgacaat | 240 |
| gaagaagtgt tgatcatgtc cgaaagcgac attctggcaa ttgttgaagc gtaa | 294 |

<210> SEQ ID NO 7
<211> LENGTH: 4524
<212> TYPE: DNA
<213> ORGANISM: Escherichia coli

<400> SEQUENCE: 7

| | |
|---|---|
| ggcgtcaccc ataacagata cggactttct caaaggagag ttatcaatga atattcgtcc | 60 |
| ttgcatgatc gcgtgatcgt caagcgtaaa gaagttgaaa ctaaatctgc tggcggcatc | 120 |
| gttctgaccg gctctgcagc ggctaaatcc acccgcggcg aagtgctggc tgtcggcaat | 180 |
| ggccgtatcc ttgaaaatgg cgaagtgaag ccgctggatg tgaaagttgg cgacatcgtt | 240 |
| attttcaacg atggctacgg tgtgaaatct gagaagatcg acaatgaaga agtgttgatc | 300 |
| atgtccgaaa gcgacattct ggcaattgtt gaagcgtaat ccgcgcacga cactgaacat | 360 |
| acgaatttaa ggaataaaga taatggcagc taaagacgta aaattcggta acgacgctcg | 420 |
| tgtgaaaatg ctgcgcggcg taaacgtact ggcagatgca gtgaaagtta ccctcggtcc | 480 |
| aaaaggccgt aacgtagttc tggataaatc tttcggtgca ccgaccatca ccaaagatgg | 540 |
| tgtttccgtt gctcgtgaaa tcgaactgga agacaagttc gaaaatatgg gtgcgcagat | 600 |
| ggtgaaagaa gttgcctcta agcaaacga cgctgcaggc gacggtacca ccactgcaac | 660 |
| cgtactggct caggctatca tcactgaagg tctgaaagct gttgctgcgg gcatgaaccc | 720 |
| gatggacctg aaacgtggta tcgacaaagc ggttaccgct gcagttgaag aactgaaagc | 780 |
| gctgtccgta ccatgctctg actctaaagc gattgctcag gttggtacca tctccgctaa | 840 |
| ctccgacgaa accgtaggta aactgatcgc tgaagcgatg gacaaagtcg gtaaagaagg | 900 |
| cgttatcacc gttgaagacg gtaccggtct gcaggacgaa ctggacgtgg ttgaaggtat | 960 |
| gcagttcgac cgtggctacc tgtctcctta cttcatcaac aagccggaaa ctggcgcagt | 1020 |
| agaactggaa agcccgttca tcctgctggc tgacaagaaa atctccaaca tccgcgaaat | 1080 |
| gctgccggtt ctggaagctg ttgccaaagc aggcaaaccg ctgctgatca tcgctgaaga | 1140 |
| tgtagaaggc gaagcgctgg caactgctgt tgttaacacc attcgtggca tcgtgaaagt | 1200 |
| cgctgcggtt aaagcaccgg gcttcggcga tcgtcgtaaa gctatgctgc aggatatcgc | 1260 |
| aaccctgact ggcggtaccg tgatctctga agagatcggt atggagctgg aaaaagcaac | 1320 |
| cctggaagac ctgggtcagg ctaaacgtgt tgtgatcaac aaagacacca ccactatcat | 1380 |
| cgatggcgtg ggtgaagaag ctgcaatcca gggccgtgtt gctcagatcc gtcagcagat | 1440 |
| tgaagaagca acttctgact acgaccgtga aaactgcag gaacgcgtag cgaaactggc | 1500 |
| aggcggcgtt gcagttatca agtgggtgc tgctaccgaa gttgaaatga agagaaaaa | 1560 |
| agcacgcgtt gaagatgccc tgcacgcgac ccgtgctgcg gtagaagaag cgtggttgc | 1620 |
| tggtggtggt gttgcgctga tccgcgtagc gtctaaactg gctgacctgc gtggtcagaa | 1680 |
| cgaagaccag aacgtgggta tcaaagttgc actgcgtgca atggaagctc cgctgcgtca | 1740 |
| gatcgtattg aactgcggcg aagaaccgtc tgttgttgct aacaccgtta aggcgcgga | 1800 |
| cggcaactac ggttacaacg cagcaaccga agaatacggc aacatgatcg acatgggtat | 1860 |
| cctggatcca accaaagtaa ctcgttctgc tctgcagtac gcagcttctg tggctggcct | 1920 |

-continued

```
gatgatcacc accgaatgca tggttaccga cctgccgaaa aacgatgcag ctgacttagg    1980
cgctgctggc ggtatgggcg gcatggggtgg catgggcggc atgatgtaat tgccctgcac   2040
ctcgcagaaa taaacaaacc ccctgtgat ttttgaggt aacaagatgc aagtttcagt     2100
tgaaaccact caaggccttg gccgccgtgt aacgattact atcgctgctg acagcatcga    2160
gaccgctgtt aaaagcgagc tggtcaacgt tgcgaaaaaa gtacgtattg acggcttccg    2220
caaaggcaaa gtgccaatga atatcgttgc tcagcgttat ggcgcgtctg tacgccagga    2280
cgttctgggt gacctgatga gccgtaactt cattgacgcc atcattaaag aaaaaatcaa    2340
tccggctggc gcaccgactt atgttccggg cgaatacaag ctgggtgaag acttcactta    2400
ctctgtagag tttgaagttt atccggaagt tgaactcgag ggtctggaag cgatcgaagt    2460
tgaaaaaccg atcgttgaag tgaccgacgc tgacgttgac ggcatgctgg atactctgcg    2520
taaacagcag gcgacctgga aagaaaaaga cggcgctgtt gaagcagaag accgcgtaac    2580
catcgacttc accggttctg tagacggcga agagttcgaa ggcggtaaag cgtctgattt    2640
cgtactggcg atgggccagg tcgtatgat cccgggcttt gaagacggta tcaaaggcca    2700
caaagctggc gaagagttca ccatcgacgt gaccttcccg gaagaatacc acgcagaaaa    2760
cctgaaaggt aaagcagcga aattcgctat caacctgaag aaagttgaag agcgtgaact    2820
gccggaactg actgcagaat tcatcaaacg tttcggcgtt gaagatggtt ccgtagaagg    2880
tctgcgcgct gaagtgcgta aaacatgga gcgcgagctg aagagcgcca tccgtaaccg    2940
cgttaagtct caggcgatcg aaggtctggt aaaagctaac gacatcgacg taccggctgc    3000
gctgatcgac agcgaaatcg acgttctgcg tcgccaggct gcacagcgtt tcggtggcaa    3060
cgaaaaacaa gctctggaac tgccgcgcga actgttcgaa aacaggcta aacgccgcgt    3120 agttgttggc ctgctgctgg gcgaagttat ccgcaccaac gagctgaaag ctgacgaaga    3180
gcgcgtgaaa ggcctgatcg aagagatggc ttctgcgtac aagatccga aagaagttat    3240 cgagttctac agcaaaaaca aagaactgat ggacaacatg cgcaatgttg ctctggaaga    3300
acaggctgtt gaagctgtac tggcgaaagc gaaagtgact gaaaaagaaa ccactttcaa    3360
cgagctgatg aaccagcagg cgtaatttac gcagcataac gcgctaaatt cgcacaaagg    3420
cccgtcaccg ccaggtggtg ggctttttt tgtcatgaat tttgcatgga accgtgcgaa    3480
aagcctcttt cggtgttagc gtaacaacaa aagattgtta tgcttgaaat atggtgatgc    3540
cgtacccata acacagggac tagctgataa tccgtccata aggttacaat cggtacagca    3600
ggttttttca atttatcca ggagacggaa atgtcataca gcggcgaacg agataacttt    3660
gcaccccata tggcgctggt gccgatggtc attgaacaga cctcacgcgg tgagcgctct    3720
tttgatatct attctcgtct acttaaggaa cgcgtcattt ttctgactgg ccaggttgaa    3780
gaccacatgg ctaacctgat tgtggcgcag atgctgttcc tggaagcaga aacccagaa    3840 aaagatatct atctgtacat taactcccca ggcggggtga tcactgccgg atgtctatc    3900 tatgacacca tgcagtttat caagcctgat gtcagcacca tctgtatggg ccaggcggcc    3960
tcgatgggcg ctttcttgct gaccgcaggg gcaaaggta aacgttttg cctgccgaat    4020 tcgcgcgtga tgattcacca accgttgggc ggctaccagg gccaggcgac cgatatcgaa    4080
attcatgccc gtgaaattct gaaagttaaa gggcgcatga atgaacttat ggcgcttcat    4140
acgggtcaat cattagaaca gattgaacgt gataccgagc gcgatcgctt cctttccgcc    4200
cctgaagcgg tggaatacgg tctggtcgat tcgattctga cccatcgtaa ttgatgccag    4260
aggcgcaact gtgccgctat acttatccag ggcggcacaa cgctgtaagc gcttgcgcct    4320
```

-continued

```
gagaatggca tttgcgtcgt cgtgtgcggc acaaagaaca aagaagaggt tttgacccat    4380
gacagataaa cgcaaagatg gctcaggcaa attgctgtat tgctcttttt gcggcaaaag    4440
ccagcatgaa gtgcgcaagc tgattgccgg tccatccgtg tatatctgcg acgaatgtgt    4500
tgatttatgt aacgacatca ttcg                                          4524
```

TRIGGER FACTOR EXPRESSION PLASMIDS

BACKGROUND OF THE INVENTION

1. Field of the Invention

The present invention relates to an artificial operon, an expression plasmid carrying the operon, a cotransformant harboring an expression vector for a foreign protein and any one of expression plasmids, and a method for producing a foreign protein comprising expressing a foreign protein by the use of the cotransformant, which are capable of expressing a foreign protein in a solubilized form and in a state of having a correct conformation.

2. Discussion of the Related Art

A trigger factor is a protein which has been found as a cytoplasmic factor required for in vitro transporting to a membrane of proOmpA, a precursor of E. coli outer membrane protein OmpA [Crooke, E. and Wickner, W., Proc. Nat. Acad. Sci. USA 84, 5216–5220 (1987)]. In addition, a tig gene has been cloned as a gene encoding a trigger factor having a molecular weight of 48 kDa [Guthrie, B. and Wickner W., J. Bacteriol. 172, 5555–5562 (1990)]. On the basis of analysis of the amino acid sequence, it has been elucidated that the trigger factor has FK506-bound protein (FKBP) domain, and that all of amino acid residues required for each expression of the binding activity with FK506 and for a peptidyl-prolyl isomerase (PPIase) activity are conserved in the trigger factor [Callebaut, I. and Mornon, J. -P., FEBS Lett. 374, 211–215 (1995)].

There has been reported that the trigger factor has been also identified as PPIase bound to 50S subunit of E. coli ribosome, and that the trigger factor markedly enhances prolyl isomerization in in vitro refolding of mutant RNase $T_1$ [Stoller, G. et al., EMBO J. 14, 4939–4948 (1995)]. Moreover, there has been found by an experiment using a crosslinking reagent that the trigger factor is bound to a nascent polypeptide chain on E. coli ribosome [Valent, Q. A. et al., EMBO J. 14, 5494–5505 (1995); Hesterkamp, T. et al., Proc. Nat. Acad. Sci. USA 93, 4437–4441 (1996)]. In addition, the trigger factor has been known to enhance binding to an unfolded protein of GroEL [Kandror, O. et al., EMBO J. 14, 6021–6027 (1995); Kandror, O. et al., J. Biol. Chem. 272, 1730–1734 (1997)].

PPIase acts on proline residue in a peptide chain, and catalyzes cis-trans isomerization of conformation regarding a peptide bond. This reaction is considered as a rate-determining step of a folding process of the protein. In addition, it is considered that the PPIase family protein is involved in protein folding, refolding, association and dissociation, transport, and the like, within the cells.

In addition, the trigger factor is shown to assist the folding of several proteins in vitro [Scholz, C. et al., EMBO J. 16, 54–58 (1997)]. However, the actual function of the trigger factor has not yet been known.

In expression of a foreign protein by E. coli, various efforts have been made on the aggregation suppression and the stabilization of a desired foreign protein by coexpression of chaperones. However, it has been difficult to predict coexpression of which of the chaperones is effective for a particular protein, so that undue experimentation is presently carried out in order to determine the effective chaperone. In addition, there are some cases where sufficient effects cannot be obtained by coexpression of known chaperones.

In view of the above problems, an object of the present invention is to provide an artificial operon comprising genes encoding each of a trigger factor, GroEL and GroES, the artificial operon being capable of expressing a foreign protein in a solubilized form and in a state of having a correct conformation.

In one embodiment, the present invention provides an expression plasmid carrying the operon and an expression plasmid for a trigger factor.

In another embodiment, the present invention provides a cotransformant harboring both of the above expression plasmid and an expression vector for a foreign protein.

In still another embodiment, the present invention provides a method for producing a foreign protein comprising expressing a foreign protein by the use of the cotransformant.

These and other objects of the present invention will be apparent from the following description.

SUMMARY OF THE INVENTION

In sum, the present invention pertains to the following:

[1] an artificial operon comprising genes encoding each of a trigger factor, GroEL and GroES;

[2] a plasmid capable of expressing each of a trigger factor, GroEL and GroES, the plasmid carrying the artificial operon according to item [1];

[3] a plasmid capable of expressing a trigger factor, the plasmid carrying a gene encoding the trigger factor under control of an inducible promoter;

[4] a cotransformant harboring the plasmid according to item [2] or [3] and an expression plasmid for a foreign protein; and

[5] a method for producing a foreign protein comprising expressing said foreign protein by the cotransformant according to item [4].

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

DETAILED DESCRIPTION OF THE INVENTION

Figure 1:
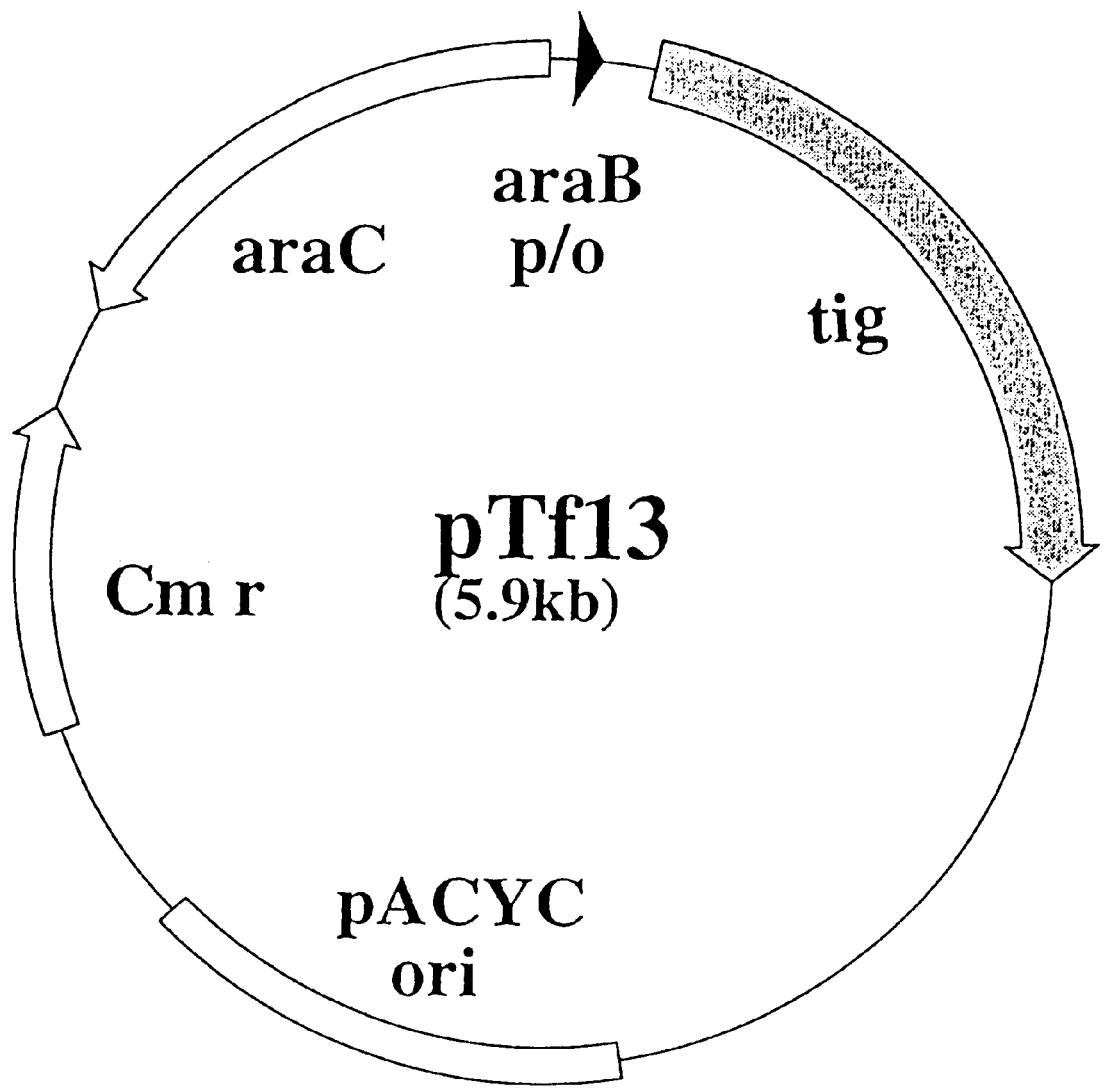
FIG. 1 is a schematic view showing pTf13 (about 5.9 kb), wherein araB p/o is araB promoter/operator, tig is a structural gene for a trigger factor, pACYC ori is an origin of replication derived from pACYC plasmid, Cmr is chloramphenicol resistance gene, and araC is araC activator/repressor, respectively.

One of the great features of the artificial operon of the present invention resides in that the operon comprising genes encoding each of a trigger factor, GroEL and GroES (the genes respectively referred to as tig gene, groEL gene and groES gene). Since the artificial operon of the present invention comprises each of tig gene, groEL gene and groES gene mentioned above, there can be exhibited an excellent effect that a soluble expression product can be efficiently obtained when the artificial operon is coexpressed with a gene encoding a foreign protein.

In the present invention, the term "trigger factor" refers to a factor which has been found as a cytoplasmic factor required for in vitro transporting to a membrane of proOmpA, a precursor of *E. coli* external membrane protein OmpA.

The trigger factor is a factor having the amino acid sequence as shown in SEQ ID NO: 1 [Guthrie, B. and Wickner, W., *J. Bacteriol.* 172, 5555–5562 (1990)]. In the present invention, the trigger factor also encompasses a factor having a sequence in which a mutation of substitution, deletion, addition or insertion of one or more amino acid residues is introduced in the amino acid sequence as shown in SEQ ID NO: 1 mentioned above, as long as the factor is capable of expressing a foreign protein in a solubilized form and in a state of having a correct conformation by coexpression with a foreign protein encoding a foreign gene.

In the artificial operon of the present invention, there can be used tig gene corresponding to an amino acid sequence of the trigger factor. The tig gene includes a gene comprising the nucleotide sequence as shown in SEQ ID NO: 2 [Guthrie, B. and Wickner, W., *J. Bacteriol.* 172, 5555–5562 (1990)]. The gene comprising the nucleotide sequence as shown in SEQ ID NO: 2 can be obtained, for instance, from Kohara Clone No. 148 [Kohara, Y. et al., *Cell* 50, 495–508 (1987)].

In addition, in the present invention, the tig gene also encompasses a gene having a sequence in which a mutation of substitution, deletion, addition or insertion of one or more bases is introduced in the nucleotide sequence as shown in SEQ ID NO: 2 mentioned above, as long as it is a gene encoding a factor capable of expressing a foreign protein in a solubilized form and in a state of having a correct conformation by coexpression with a foreign gene.

Further, in the present invention, the tig gene also encompasses a gene comprising a DNA capable of hybridizing under stringent conditions to any one of DNAs selected from the group consisting of a DNA comprising the nucleotide sequence as shown in SEQ ID NO: 2 and a DNA having a sequence in which a mutation of substitution, deletion, addition or insertion of one or more bases is introduced in the nucleotide sequence as shown in SEQ ID NO: 2 mentioned above, as long as it is a gene encoding a factor capable of expressing a foreign protein in a solubilized form and in a state of having a correct conformation by coexpression with a foreign gene.

The conditions for hybridization include conditions described, for instance, in *Molecular Cloning: A Laboratory Manual*, 2nd Ed. [Sambrook, J. et al., Cold Spring Harbour Laboratory Press, New York (1989)], and the like.

The amino acid sequences for GroEL and GroES usable in the present invention are shown in SEQ ID NOs: 3 and 4, respectively [Hemmingsen, S. M. et al., *Nature* 333, 330–334 (1988)]. In the present invention, GroEL and GroES also encompass factors each having a sequence in which a mutation of substitution, deletion, addition or insertion of one or more amino acid residues is introduced in each of the amino acid sequences as shown in SEQ ID NOs: 3 and 4 mentioned above, as long as the factors have equivalent functions to wild-type GroEL and GroES each having the sequence as shown in SEQ ID NOs: 3 and 4 mentioned above, respectively.

The groEL gene and the groES usable in the present invention gene include genes comprising each of the nucleotide sequences as shown in SEQ ID NOs: 5 and 6, respectively [Hemmingsen, S. M. et al., *Nature* 333, 330–334 (1988)]. Each of the groEL gene and the groES gene can be obtained, for instance, from pGro11 plasmid [Nishihara, K. et al., *Appl. Environ. Microbiol.* 64, 1694–1699 (1988)].

In the present invention, the groEL gene and the groES gene encompass genes each having a sequence in which a mutation of substitution, deletion, addition or insertion of one or more bases is introduced in each of the nucleotide sequences as shown in SEQ ID NOs: 5 and 6 mentioned above, as long as each of the genes encodes a factor having an equivalent function to wild-type GroEL and GroES mentioned above.

Further, the groEL gene and the groES gene also encompass genes each comprising a DNA capable of hybridizing under stringent conditions to any one of DNAs selected from the group consisting of a DNA comprising the nucleotide sequence as shown in SEQ ID NO: 5 or 6 and a DNA having a sequence in which a mutation of substitution, deletion, addition or insertion of one or more bases is introduced in the nucleotide sequence as shown in SEQ ID NO: 5 or 6 mentioned above, as long as each of the genes encodes a factor having an equivalent function to wild-type GroEL and GroES mentioned above.

In the artificial operon of the present invention, the arrangement of the tig gene, the groEL gene and the groES gene is not particularly limited. Examples thereof include an operon arranged sequentially as groES-groEL-tig, and the like.

In the artificial operon of the present invention, the tig gene, the groEL gene and the groES gene can be localized under the control of a promoter.

The promoter for controlling the transcription of the operon existing under the control of the promoter is preferably an inducible promoter, from the viewpoint of regulating each of the expression levels of a trigger factor, GroEL and GroES. Examples of the inducible promoter include, for instance, lac, tac, trc, trp, ara, Pzt-1, $P_L$ and T7. Each of the lac, tac and trc promoters can be induced by using isopropyl-β-D-thiogalactopyranoside (IPTG); each of the trp, ara and Pzt-1 promoters can be induced with 3-indoleacrylic acid (IAA), L-arabinose and tetracycline, respectively; and the $P_L$ promoter can be induced at a high temperature (42° C.). Also, the T7 promoter, which is specifically and strongly transcribed by T7 RNA polymerase, can be used. In this case, the T7 promoter can be induced with IPTG by using an *E. coli* strain harboring a lysogenized λ phage carrying the T7 RNA polymerase gene ligated downstream of the lac promoter is used. Among the promoters, from the viewpoint of facilitating the manipulations for induction, lac, trp, ara and Pzt-1 are preferable. The promoter is contained in a known vector, and it can be used by appropriately cutting out from the vector by using a restriction enzyme, and the like.

In addition, in the artificial operon of the present invention, a factor encoded by an artificial operon can be more stably expressed by possessing a terminator represented by, for instance, rrnBT1T2. The terminator is contained in a known vector, and it can be used by appropriately cutting out from the vector by using a restriction enzyme, and the like.

Concrete examples of the artificial operon of the present invention include, for instance, an operon comprising the nucleotide sequence as shown in SEQ ID NO: 7.

One of the great features of the plasmid of the present invention resides in that the plasmid carries a gene encoding a trigger factor, or it carries the artificial operon.

In the plasmid of the present invention, it is preferable that a factor encoded by a gene encoding a trigger factor, or factors (trigger factor, GroEL and GroES) encoded by an artificial operon can be expressed by using an inducible promoter.

In addition, when the plasmid of the present invention is introduced into a host, there may be used a desired foreign protein and a plasmid carrying a gene encoding a trigger factor, or a gene encoding the operon on the same plasmid. In addition, there may be used simultaneously a plasmid carrying a gene encoding a trigger factor or a gene encoding the operon, and a plasmid carrying a gene encoding a foreign protein (hereinafter referred to as "coexpression plasmid"). Among these plasmids, the coexpression plasmid is preferable from the viewpoints of not necessitating to prepare for each foreign protein a plasmid carrying a desired foreign protein and a gene encoding a trigger factor or a gene encoding the operon, and the stability of the plasmid in a host.

In order to optimize the expression level and the expression timing of the trigger factor or factors encoded by the artificial operon, without lowering the expression level of the foreign protein, it is advantageous that the expression of the trigger factor or the factors encoded by the artificial operon can be independently regulated from expression of a desired protein. From the above aspects, it is preferable that the inducible promoters used in expression of the trigger factor or the factors encoded by the artificial operon are different from the promoter usable in expression of a desired protein.

When a coexpression plasmid is used as the plasmid, any expression vector can be used, as long as it carries a replicon which does not exhibit incompatibility with an expression vector of a desired protein in a host used, including, for instance, *E. coli*. For instance, when a vector carrying ColE1 replicon, the vector including, for instance, pBR322 is used as an expression vector for a desired protein, the plasmid used in expression of the trigger factor or the factors encoded by the artificial operon includes p15A replicon existing in pACYC plasmid derivatives.

Figure 2:
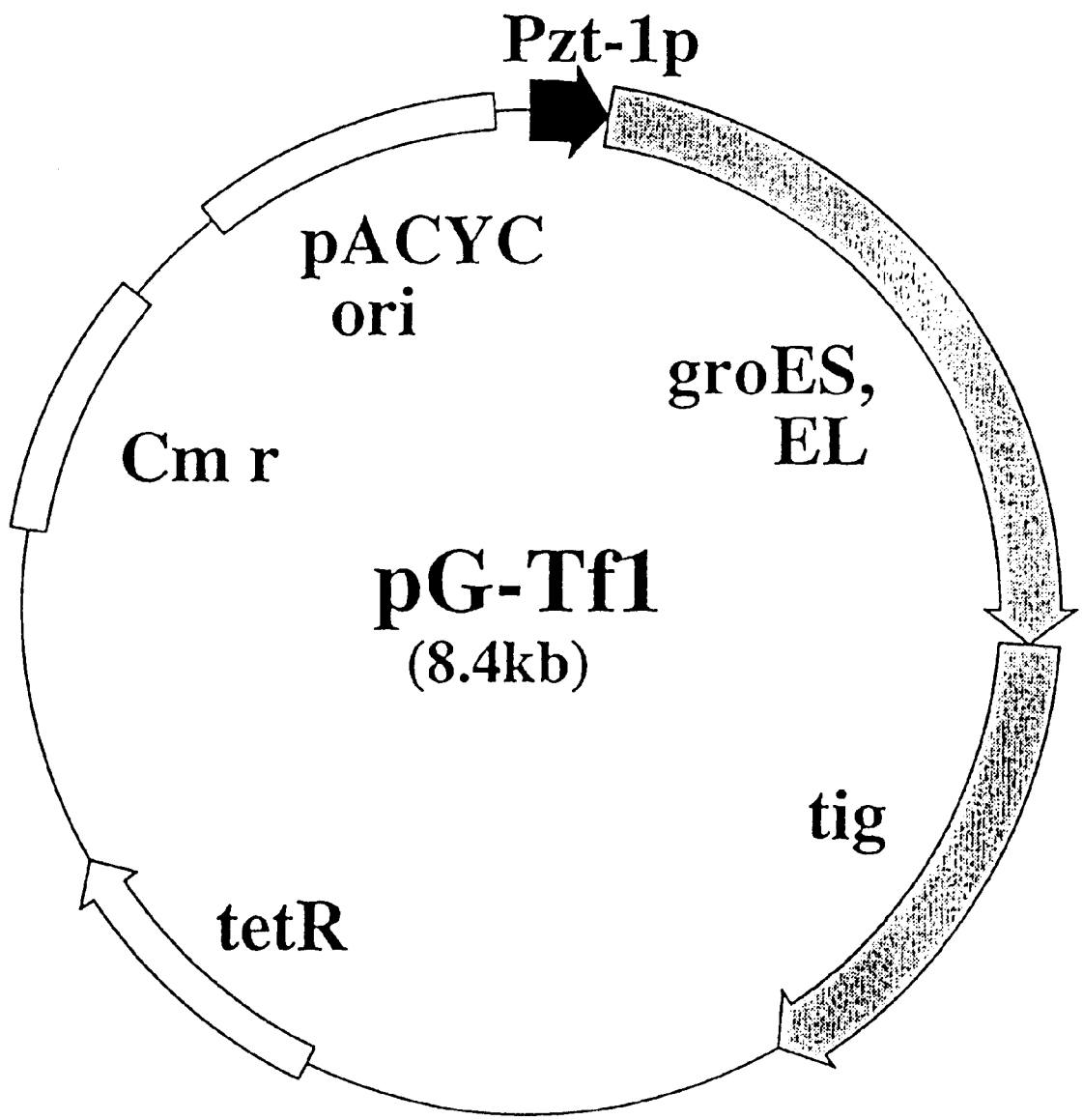
FIG. 2 is a schematic view showing pG-Tf1 (about 8.4 kb), wherein Pzt-1p is Pzt-1 promoter, groES and groEL are genes each encoding GroES and GroEL, tig is a structural gene for a trigger factor, tetR is tetR repressor, Cmr is chloramphenicol resistance gene, and pACYC ori is an origin of replication of pACYC plasmid, respectively.

Concrete examples of the expression plasmid of the present invention include coexpression plasmids pTf13 and pG-Tf1. Schematic views of each of these coexpression plasmids are shown in FIGS. 1 and 2, respectively.

Each of pTf13 and pG-Tf1 can be obtained by, for instance, the procedures set forth in Examples 1 and 2 below.

The cotransformant of the present invention can be obtained by introducing the plasmid of the present invention (coexpression plasmid) and an expression vector for a foreign protein into an appropriate host.

The expression vector for a foreign protein used in the cotransformant described above is not particularly limited. The vector includes a vector being capable of expressing in the cytosol of cells of a desired foreign protein or secreting in the periplasm of cells, and exhibiting compatibility with the coexpression plasmid. In particular, those vectors in which expression of a desired foreign protein is induced by an inducible promoter are preferable. The inducible promoter includes the same promoters as those listed above. The trigger factor or the factors encoded by an artificial operon can be induced to be expressed independently from a desired foreign protein by selecting a promoter other than the promoter used in the induction of expression of the trigger factor or the factors encoded by an artificial operon.

In addition, the expression vector for a foreign protein may carry a selection marker gene as occasion demands. Examples of such selection marker genes include ampicillin resistance (Amp$^r$) genes, kanamycin resistance (Km$^r$) genes, and chloramphenicol resistance (Cm$^r$) genes. A double selection of the cotransformant can be made possible by using a selection marker gene different from that contained in the plasmid (coexpression plasmid) of the present invention.

The expression vector for a foreign protein is preferably a vector capable of secreting to the periplasm of cells, from the viewpoint of correct formation of disulfide bonds in the resulting foreign protein. Examples of the expression vector include, for instance, a vector carrying a gene encoding a polypeptide resulting from addition of a signal peptide, such as OmpA, OmpT, MalE or β-lactamase, to a desired foreign protein. The expression vector can be obtained, for instance, by adding a gene encoding the signal peptide to a site corresponding to N-terminus of a desired foreign protein by genetic engineering techniques, and incorporating the resulting gene into a known vector.

In addition, in the expression vector of a foreign protein of the present invention, there may be contained a sequence which can facilitate purification of a desired protein, as represented by, for instance, expression as a fusion protein with a protein such as β-galactosidase, glutathione-S-transferase or a maltose-bound protein; expression as histidine-tagged proteins, or the like.

The host usable in the present invention includes, for instance, *E. coli* strains. Concrete examples of the strains include generally employed strains such as HB101, JM109, MC4100, MG1655 and W3110; and various mutants, including protease mutants such as degP mutants, ompT mutants, tsp mutants, lon mutants, clpPX mutants, hslV/U mutants, lon-clpPX double mutants and lon-clpPX-hslV/U triple mutants; plsX mutants; rpoH mutants such as rpoH deletion mutants and rpoH missense mutants, and the like.

In the present invention, protease mutants, such as lon-clpPX double mutants and lon-clpPX-hslV/U triple mutants; plsX mutants; and rpoH mutants, can be favorably used, from the viewpoint of more stably expressing the foreign protein. Among the rpoH mutants, rpoH deletion mutants are preferable, from the viewpoint of more stably expressing the foreign protein.

Here, a preferable lon-clpPX double mutant is KY2783 strain derived from *E. coli* strain W3110, the KY2783 resulting from introduction of double deletion mutations in the lon and clpPX genes. The KY2783 strain was named and identified as *E. coli* KY2783 and has been deposited under accession number FERM BP-6244 with the National Institute of Bioscience and Human-Technology, Agency of Industrial Science and Technology, Ministry of International Trade and Industry, of which the address is 1-3, Higashi 1-chome, Tsukuba-shi, Ibaraki-ken, 305-8566, Japan; date of original deposit: Feb. 3, 1998.

Also, the term "lon-clpPX-hslV/U triple mutant" refers to a mutant prepared by further mutating hslV/U gene encoding HslV/U protease, in the above-described lon-clpPX double mutant. A preference is given to KY2893 strain derived from *E. coli* strain W3110, the KY2893 strain resulting from introduction of triple deletion mutations in the lon, clpPX and hslV/U genes. The KY2893 strain was named and deposited *E. coli* KY2893 strain and has been deposited under accession number FERM BP-6243 with the National Institute of Bioscience and Human-Technology, Agency of Industrial Science and Technology, Ministry of International Trade and Industry, of which the address is 1-3, Higashi 1-chome, Tsukuba-shi, Ibaraki-ken, 305-8566, Japan; date of original deposit: Feb. 3, 1998.

The foreign protein to be expressed in the present invention may be any protein, as long as it is a foreign protein capable of being instabilized and/or insolubilized in *E. coli*. Concrete examples of the foreign proteins include interferons, interleukins, interleukin receptors, interleukin receptor antagonists, granulocyte colony-stimulating factors, granulocyte macrophage colony-stimulating factors, macrophage colony-stimulating factors, erythropoietin, thrombopoietin, leukemia inhibitory factors, stem cell growth factors, tumor necrosis factors, growth hormones, proinsulin, insulin-like growth factors, fibroblast growth factors, platelet-derived growth factors, transforming growth factors, hepatocyte growth factors, osteogenic factors, nerve growth factors, ciliary neurotrophic factors, brain-derived neurotrophic factors, glial-derived neurotrophic factors, neurotrophine, angiogenesis inhibitors, prourokinase, tissue plasminogen activators, blood coagulation factors, protein C, glucocerebrosidase, superoxide dismutase, renin, lysozyme, P450, prochymosin, trypsin inhibitors, elastase inhibitors, lipocortin, reptin, immunoglobulins, single-chain antibodies, complement components, serum albumin, cedar pollen allergens, hypoxia-induced stress proteins, protein kinases, proto-oncogene products, transcription regulation factors and virus-constituent proteins.

The method for introducing the plasmid of the present invention into *E. coli* together with an expression vector for a foreign protein includes a usual method, such as calcium chloride method, rubidium chloride method or electroporation method. The cotransformant can be screened by using a reagent depending on the selection marker gene. Expression of the foreign protein can be confirmed, for instance, by Western blott analysis.

One of the great features of the method for producing a foreign protein resides in that the method comprises expressing the foreign protein by the use of the cotransformant described above. The foreign protein can be produced by, for instance, a process comprising culturing a transformant under induction conditions in which the expression level of the trigger factor or the expression level of each of trigger factor, GroEL and GroES is each at a level appropriate for stabilization and/or solubilization of a foreign protein to be expressed; harvesting the cells; disrupting the harvested cells; isolating and purifying the foreign protein from the disrupted cell solution in accordance with the purification method depending upon the desired foreign protein.

The induction conditions differ depending upon the inducible promoters used for the plasmid of the present invention and the expression vector for a foreign protein, as long as the conditions are such that the expression level of the trigger factor or the expression level of each of trigger factor, GroEL and GroES is each at a level appropriate for stabilization and/or solubilization of the foreign protein. For instance, the induction conditions can be determined as follows.

First, the inductive substance of the promoter is added with varying various addition concentrations and the timing for addition. The cells in which the foreign protein is expressed are harvested, and each of the harvested cells is disrupted, to give a cell free extract. Each of the resulting extract is subjected to, for instance, SDS-PAGE, and subsequently the bands ascribed to proteins in the gel is visualized by Coomassie brilliant blue staining or silver staining. Among the visualized bands, appropriate induction conditions for the band ascribed to a foreign protein can be examined by determining the concentration of the band by densitometry or other means.

The culture conditions of the cotransformant differs depending upon the cells used as a host, and it is not particularly limited. The level of expressed foreign protein can be determined in the same manner as the determination of the induction conditions by setting various culture time periods and culture temperatures to express the foreign protein under each culture conditions.

The method for isolation and purification of a foreign protein includes, for instance, purification methods for protein as represented by salting-out, ion-exchange chromatography, hydrophobic chromatography, affinity chromatography, gel filtration chromatography and the like.

EXAMPLES

The present invention will be hereinafter described in more detail by means of the following examples, without intending to restrict the scope or spirit of the present invention thereto.

Example 1

Construction of pTf13

A fragment of about 2.6 kb carrying tig gene was cut out with XmnI and NruI from Kohara Clone No. 148 [Kohara, Y. et al., *Cell* 50, 495–508 (1987)] comprising a trigger factor, and thereafter the resulting XmnI-NruI fragment was blunt-ended, to give a tig gene fragment. pAR3 Plasmid [Perez—Perez, J. & Guitierrez, J., *Gene* 158, 141–142 (1995)] was cleaved with PstI, and thereafter the resulting linearized plasmid fragment was blunt-ended, to give a pAR3 fragment. The tig gene fragment obtained as above was ligated to the pAR3 fragment, whereby constructing pTf13.

Example 2

Construction of pG-Tf1

A fragment of about 2.5 kb carrying tig gene was cut out with Bsp1286II and NruI from Kohara Clone No. 148 mentioned above, and thereafter the resulting Bsp1286II-NruI fragment was blunt-ended, to give a tig gene fragment. pGro11 plasmid [Nishihara, K. et al., *Appl. Environ. Microbiol.* 64, 1694–1699 (1988)] was cleaved with SmaI at downstream of groEL gene, and thereafter the resulting blunt-ended tig gene fragment was ligated to the linearized plasmid fragment, to give pG-Tf1.

Preparation Example 1

Preparation of Cotransformant for Expression of Murine Endostatin

*E. coli* BL21 was transformed with pTB01#8 [O'Reilly, M. S. et al., *Cell* 88, 277–285 (1997); made available from Dr. Thomas Boehm and Dr. Judah Folkman of Children's Hospital, Harvard Medical School] (50 ng) encoding murine endostatin and one of pTf13 or pG-Tf1 (each being 50 ng), to give a cotransformant. Here, the transformation was carried out by calcium chloride method.

The cotransformant harboring pTf13 and pTB01#8 was obtained by screening with a plate containing chloramphenicol and ampicillin at concentrations of 20 μg/ml and 50 μg/ml, respectively. The resulting clone in which the trigger factor was coexpressed with the murine endostatin was named NK365.

The cotransformant harboring pG-Tf1 and pTB01#8 was obtained by screening with a plate containing chloramphenicol and ampicillin at concentrations of 20 μg/ml and 50 μg/ml, respectively. The resulting clone in which the trigger factor, GroEL and GroES were coexpressed with the murine endostatin was named NK364.

As a comparative example, each of cotransformants, one in which GroEL and GroES were coexpressed with murine endostatin; one in which DnaK, DnaJ and GrpE were coexpressed with murine endostatin; and one in which DnaK, DnaJ, GrpE, GroEL and GroES were coexpressed with murine endostatin, was prepared, respectively.

The clone in which DnaK, DnaJ, GrpE, GroEL and GroES were coexpressed with murine endostatin was obtained by cotransforming with pG-KJE8 and pTB01#8, and screening with a plate containing chloramphenicol and ampicillin at concentrations of 20 μg/ml and 50 μg/ml, respectively. The resulting clone was named NK363.

pG-KJE8 was prepared in the manner described below with a plasmid which was capable of regulating chaperone expression more tightly by inserting rrnBT1T2 terminator sequence at downstream of dnaK-dnaJ-grpE gene in pG-KJE6 [Nishihara, K. et al., *Appl. Environ. Microbiol.* 64, 1694–1699 (1988)]. First, pKJE7 was cleaved with KpnI at the KpnI site located downstream of dnaK-dnaJ-grpE gene, to give a linearized KpnI-fragment, and thereafter the resulting KpnI-fragment was blunt-ended. Next, rrnBT1T2 sequence cut out from pTrc99A (manufactured by Pharmacia) at the XmnI site was ligated to the blunt-ended fragment, whereby giving plasmid pKJE9. Subsequently, pKJE9 was cleaved at the XmnI site, and blunt-ended tetR-Pzt1p-groES-groEL fragment was inserted in the same manner as the case where pG-KJE6 was prepared. A plasmid in which tetR-Pzt1p-groES-groEL fragment was inserted in the same orientation as pG-KJE6 was selected, and the plasmid was named pG-KJE8.

Test Example 1

Expression of Murine Endostatin

Expression of murine endostatin was examined using each of the cotransformants obtained in Preparation Example 1. The cultivation was carried out using L medium (composition: 1% bactotrypton, 0.5% yeast extract, 0.5% NaCl, 20 μg/ml chloramphenicol and 50 μg/ml ampicillin).

Each of the cotransformants was cultured at 37° C. Expression of the chaperone was induced by adding L-arabinose (final concentration: 10 mg/ml) to a medium for NK365 at the beginning of cultivation. Alternatively, expression of the chaperone was induced by adding tetracycline (final concentration: 10 ng/ml) to a medium for NK364. Subsequently, when Klett Unit was about 60, expression of endostatin was induced by adding 10 mM MgSO$_4$ and 3×10$^9$ pfu/ml λ-phage CE6 (manufactured by Novagen) to a cultured medium.

Expression of GroEL and GroES together with murine endostatin was induced by adding tetracycline (50 ng/ml) at the beginning of cultivation for NK363, and adding 10 mM MgSO$_4$ and λ-phage CE6 in the same manner as above to a cultured medium when Klett Unit was about 60.

In addition, expression of DnaK, DnaJ and GrpE together with murine endostatin was induced by adding L-arabinose (10 mg/ml) at the beginning of cultivation, and adding each of MgCl$_2$ and λ-phage CE6 to a cultured medium when Klett Unit was about 60.

Further, expression of DnaK, DnaJ, GrpE, GroEL and GroES together with murine endostatin was induced by adding L-arabinose (10 mg/ml) and tetracycline (20 ng/ml) at the beginning of cultivation, and adding each of MgCl$_2$ and λ-phage CE6 to a cultured medium when Klett Unit was about 60.

After the induction of expression of endostatin was carried out for 2 hours, the cells were harvested. The resulting cells were subjected to ultrasonic disruption, and thereafter the disrupted cells were centrifuged at 8200×g, thereby separating a soluble fraction from an insoluble fraction. Each of the fractions was subjected to SDS-PAGE in an amount of 8 μg equivalent of cellular protein. Here, a fraction obtained from NK365, which does not induce expression of the trigger factor, was used as a control. The results are shown in FIG. 3.

Figure 3:
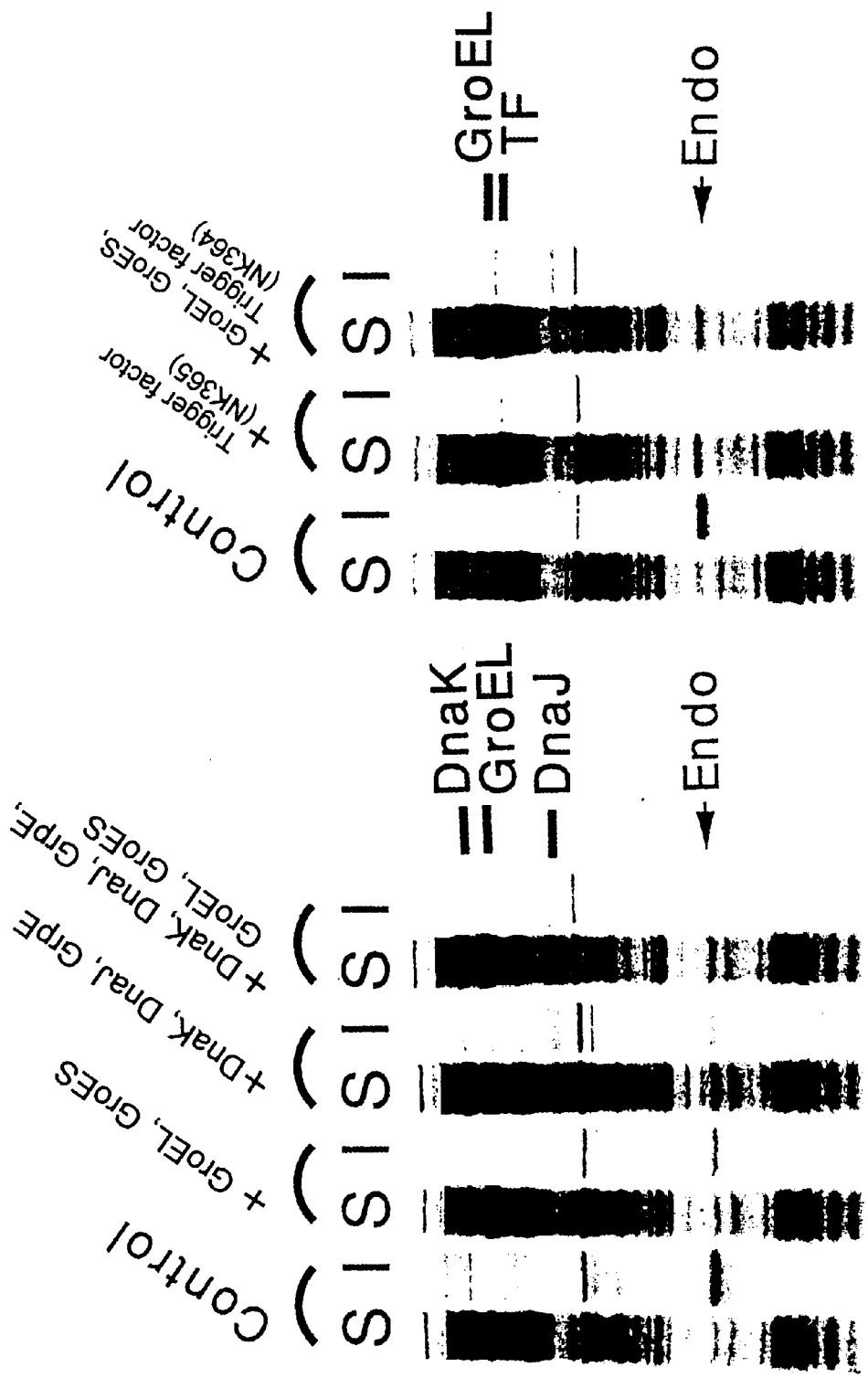
FIG. 3 shows the analytical results on SDS-PAGE of solubilization of murine endostatin by coexpression with a trigger factor, wherein S is a soluble fraction, and I is an insoluble fraction.

As shown in the left panel of FIG. 3, in the case of coexpressing murine endostatin which is usually insolubilized to be expressed as inclusion bodies in *E. coli*, with GroEL and GroES, the majority of endostatin was detected in the soluble fraction, but some murine endostatin was also detected in the insoluble fraction. Further, also in the case of coexpressing murine endostatin with DnaK, DnaJ and GrpE or coexpressing murine endostatin with DnaK, DnaJ, GrpE, GroEL and GroES, murine endostatin was detected in the insoluble fraction.

On the other hand, from the results in the right panel of FIG. 3, in both cases of coexpressing murine endostatin with the trigger factor, and coexpressing murine endostatin with the trigger factor, GroEL and GroES, the expressed endostatin was detected only in the soluble fraction, but not detected in the insoluble fraction. In addition, as compared with the control in which there was no coexpression of a foreign protein together with the trigger factor, or with the trigger factor, GroEL and GroES, it was observed that the soluble fraction was increased.

As described above, as compared with coexpression of each of chaperones GroEL and GroES; DnaK, DnaJ and GrpE; and DnaK, DnaJ, GrpE, GroEL and GroES, an unexpectedly excellent solubilization effect of a foreign protein can be obtained by coexpression with the trigger factor, or with the trigger factor, GroEL and GroES.

Preparation Example 2

Preparation of Cotransformant for Human ORP150 Expression

*E. coli* JM109 was transformed with plasmid pORP4 (50 ng) encoding human ORP150 and each (50 ng each) of pTf13 or pG-Tf1 obtained in Example 1 or 2, and pGro1, which is a plasmid harboring groEL and groES [Nishihara, K. et al., *Appl. Environ. Microbiol.* 64, 1694–1699 (1988)]. Here, the transformation was carried out by calcium chloride method.

The cotransformant of pTf13 and pORP4 was obtained by screening with a plate containing chloramphenicol and ampicillin at concentrations of 20 μg/ml and 50 μg/ml, respectively. The resulting clone was named NK360.

The cotransformant of pG-Tf1 and pORP4 was obtained by screening with a plate containing chloramphenicol and ampicillin at concentrations of 20 μg/ml and 50 μg/ml, respectively. The resulting clone was named NK340.

The cotransformant of pGro11 and pORP4 was obtained by screening with a plate containing chloramphenicol and ampicillin at concentrations of 20 µg/ml and 50 µg/ml, respectively. The resulting clone was named NK341.

Test Example 2

Human ORP150 Expression

Expression of human ORP150 was examined for each of NK360, NK340 and NK341 obtained in Preparation Example 2. The cultivation was carried out using L medium (composition: 1% bactotrypton, 0.5% yeast extract, 0.5% NaCl, 20 µg/ml chloramphenicol and 50 µg/ml ampicillin).

Each of the cotransformants was cultured at 37° C. Expression of the chaperone and ORP150 was induced by adding tetracycline (final concentration: 10 ng/ml) and IPTG (final concentration: 1 mM) to each of the cultured media of NK340 and NK341, when Klett Unit reached about 40. Expression of the trigger factor was induced by adding L-arabinose (final concentration: 10 mg/ml) to a cultured medium of NK360, when Klett Unit reached about 20. Subsequently, expression of ORP150 was induced by adding IPTG (final concentration: 1 mM) thereto, when Klett Unit reached about 40.

Two hours after addition of IPTG, each of the cells was harvested. The resulting cells were subjected to ultrasonic disruption, and thereafter the disrupted cells were centrifuged at 8200×g, thereby separating a soluble fraction from an insoluble fraction. Each of the fractions was subjected to SDS-PAGE in an amount of 8 µg equivalent of cellular protein. Here, a fraction obtained from NK341, which does not induce expression of the chaperones (GroEL, GroES), was used as a control. The results are shown in FIG. 4.

Figure 4:
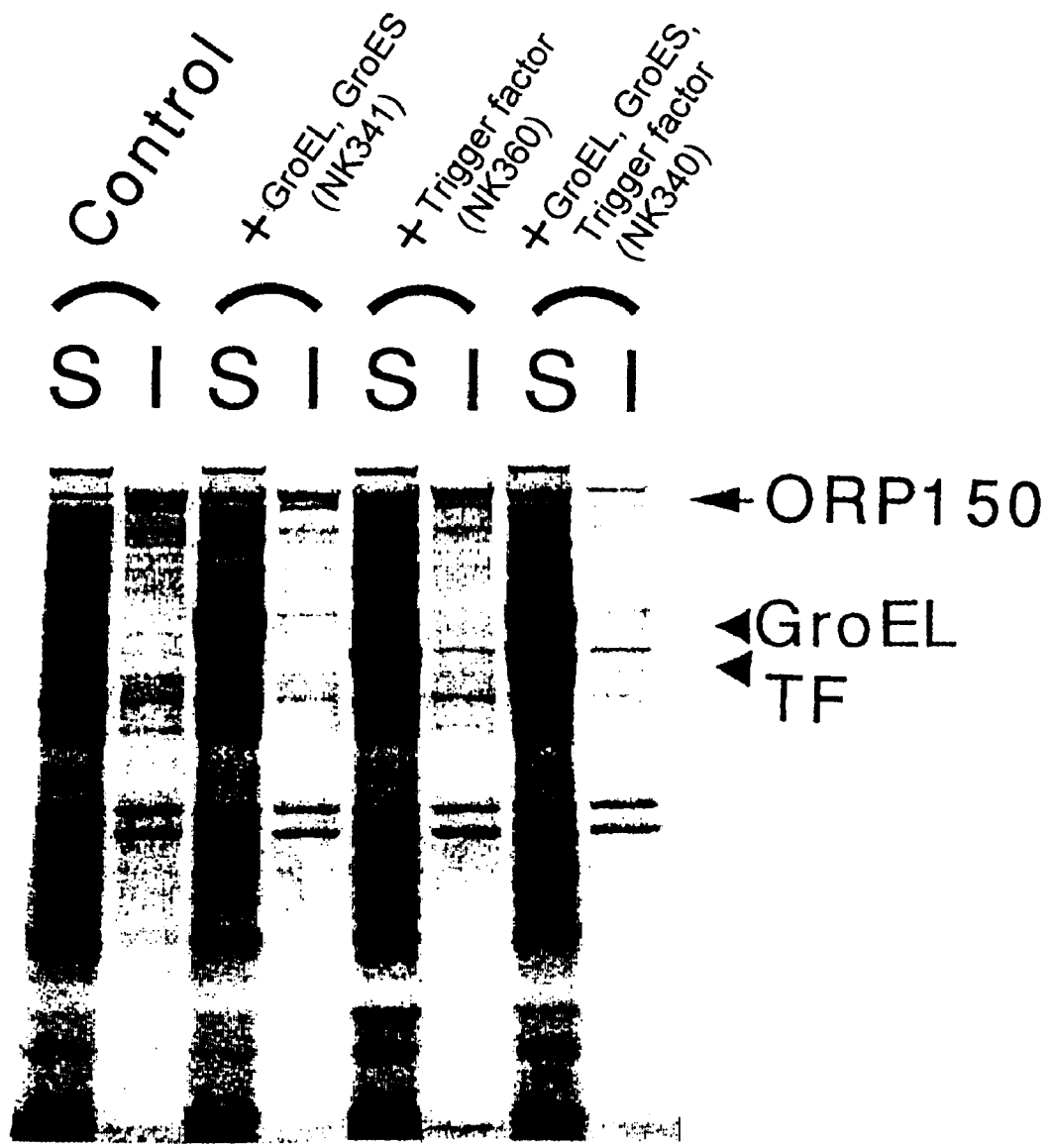
FIG. 4 shows the analytical results on SDS-PAGE of solubilization of human ORP150 by coexpression with a trigger factor, wherein S is a soluble fraction, and I is an insoluble fraction.

From the results of FIG. 4, it is shown that a half amount of expressed ORP150 becomes soluble by coexpressing ORP150, which is usually insolubilized to be expressed as inclusion bodies in *E. Coli*, with GroEL and GroES or with the trigger factor, and that substantially all of ORP150 become soluble by coexpression with GroEL, GroES and the trigger factor.

The artificial operon and the plasmid of the present invention exhibit excellent properties in that the foreign protein can be expressed in a stabilized state and a solubilized state by coexpression of a desired foreign gene. In addition, the cotransformant of the present invention exhibits an excellent effect in that the foreign protein can be expressed in a stabilized state and a solubilized state. Further, according to a method for producing a foreign protein of the present invention, there can be exhibited an excellent effect that the foreign protein can be expressed in a stabilized state and a solubilized state. According to the present invention, it is made possible to efficiently produce a foreign protein in *E. coli* by genetic engineering techniques.

What is claimed is:

1. An artificial operon comprising genes encoding each of a trigger factor, GroEL and GroES.

2. The artificial operon according to claim 1, further comprising an inducible promoter.

3. The artificial operon according to claim 2, wherein said inducible promotor is selected from the group consisting of lac, trp, ara and Pzt-1.

4. A plasmid, comprising:
the artificial operon according to any one of claims 1 to 3.

5. A cotransformant harboring the plasmid according to claim 4 and an expression plasmid for a foreign protein.

6. The cotransformant according to claim 5, obtainable by using a protease mutant of *E. coli* as a host.

7. The cotransformant according to claim 5, obtainable by using a plsX mutant of *E. coli* as a host.

8. The cotransformant according to claim 5, obtainable by using an rpoH mutant of *E. coli* as a host.

9. The cotransformant according to claim 6, wherein the protease mutant is a lon-clpPX double mutant or a lon-clpPX-hslV/U triple mutant.

10. The cotransformant according to claim 8, wherein said rpoH mutant is an rpoH deletion mutant.

11. The cotransformant according to any one of claims 5 to 10, wherein said foreign protein is selected from the group consisting of interferons, interleukins, interleukin receptors, interleukin receptor antagonists, granulocyte colony-stimulating factors, granulocyte macrophage colony-stimulating factors, macrophage colony-stimulating factors, erythropoietin, thrombopoietin, leukemia inhibitory factors, stem cell growth factors, tumor necrosis factors, growth hormones, proinsulin, insulin-like growth factors, fibroblast growth factors, platelet-derived growth factors, transforming growth factors, hepatocyte growth factors, osteogenic factors, nerve growth factors, ciliary neurotrophic factors, brain-derived neurotrophic factors, glial-derived neurotrophic factors, neurotrophine, angiogenesis inhibitors, prourokinase, tissue plasminogen activators, blood coagulation factors, protein C, glucocerebrosidase, superoxide dismutase, renin, lysozyme, P450, prochymosin, trypsin inhibitors, elastase inhibitors, lipocortin, reptin, immunoglobulins, single-chain antibodies, complement components, serum albumin, cedar pollen allergens, hypoxia-induced stress proteins, protein kinases, proto-oncogene products, transcription regulation factors and virus-constituent proteins.

12. A method for producing a foreign protein comprising:
culturing the cotransformant according to claim 11; and
isolating said foreign protein.

13. The method according to claim 12, wherein the cotransformant is cultured under induction conditions which result in the trigger factor, or each of the trigger factor, GroEL and GroES being expressed at a level suitable for increased solubilization of the foreign protein relative to the host transformed with a plasmid for expression of said foreign protein alone.

14. The method according to claim 12, wherein said foreign protein is murine endostatin or human ORP150.

15. A cotransformant harboring a plasmid comprising
a gene encoding a trigger factor under control of an inducible promoter, and
an expression plasmid for a foreign protein.

16. The cotransformant according to claim 15, wherein said inducible promoter is selected from the group consisting of lac, trp, ara and Pzt-1.

17. The cotransformant according to claim 15, obtainable by using a protease mutant of *E. coli* as a host.

18. The cotransformant according to claim 15, obtainable by using a plsX mutant of *E. coli* as a host.

19. The cotransformant according to claim 15, obtainable by using a rpoH mutant of *E. coli* as a host.

20. The cotransformant according to claim 17, wherein the protease mutant is a lon-clpPX double mutant or a lon-clpPX-hslV/U triple mutant.

21. The cotransformant according to claim 19, wherein said rpoH mutant is a rpoH deletion mutant.

22. The cotransformant according to any one of claims 15 to 21, wherein said foreign protein is selected from the group consisting of interferons, interleukins, interleukin receptors, interleukin receptor antagonists, granulocyte colony-stimulating factors, granulocyte macrophage colony-stimulating factors, macrophage colony-stimulating factors, erythropoietin, thrombopoietin, leukemia inhibitory factors, stem cell growth factors, tumor necrosis factors, growth hormones, proinsulin, insulin-like growth factors, fibroblast growth factors, platelet-derived growth factors, transforming growth factors, hepatocyte growth factors, osteogenic factors, nerve growth factors, ciliary neurotrophic factors, brain-derived neurotrophic factors, glial-derived neurotrophic factors, neurotrophine, angiogenesis inhibitors, prourokinase, tissue plasminogen activators, blood coagulation factors, protein C, glucocerebrosidase, superoxide dismutase, renin, lysozyme, P450, prochymosin, trypsin inhibitors, elastase inhibitors, lipocortin, reptin, immunoglobulins, single-chain antibodies, complement components, serum albumin, cedar pollen allergens, hypoxia-induced stress proteins, protein kinases, proto-oncogene products, transcription regulation factors, and virus-constituent proteins.

23. A method for producing a foreign protein comprising:
culturing the cotransformant according to claim 22, and
isolating said foreign protein.

24. The method according to claim 23, wherein the cotransformant is cultured under induction conditions which result in the trigger factor being expressed at a level suitable for increased solubilization of the foreign protein relative to the host transformed with a plasmid for expression of said foreign protein alone.

25. The method according to claim 23, wherein said foreign protein is murine endostatin or human ORP150.

* * * * *